(12) United States Patent
Bhatnagar et al.

(10) Patent No.: US 7,223,758 B2
(45) Date of Patent: May 29, 2007

(54) PYRIDAZINE DERIVATIVE, PHARMACEUTICAL COMPOSITION THEREOF, ITS PHARMACEUTICAL USE, AND PROCESS FOR ITS PREPARATION

(75) Inventors: Neerja Bhatnagar, Savigny sur Orge (FR); Didier Benard, Bouffemont (FR); Jean-Francois Gourvest, Claye Souilly (FR); Jacques Mauger, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/916,175

(22) Filed: Aug. 11, 2004

(65) Prior Publication Data

US 2005/0165017 A1    Jul. 28, 2005

Related U.S. Application Data

(63) Continuation of application No. PCT/FR03/00381, filed on Feb. 7, 2003.

(30) Foreign Application Priority Data

Feb. 11, 2002  (FR) .................................. 02 01632

(51) Int. Cl.
| | |
|---|---|
| *C07D 413/12* | (2006.01) |
| *C07D 413/14* | (2006.01) |
| *A61K 31/501* | (2006.01) |
| *A61P 19/02* | (2006.01) |

(52) U.S. Cl. .............. 514/236.5; 514/247; 514/252.01; 544/115; 544/224; 544/238

(58) Field of Classification Search ................ 544/115, 544/238, 224; 514/236.5, 252.01, 247
See application file for complete search history.

(56) References Cited

U.S. PATENT DOCUMENTS 5,643,908 A    7/1997  Sugimura et al.

*Primary Examiner*—Kahsay Habte
(74) *Attorney, Agent, or Firm*—Jiang Lin; Raymond S. Parker, III

(57) ABSTRACT

The invention relates to a pyridazine derivative of formula (I), wherein the variables are as defined

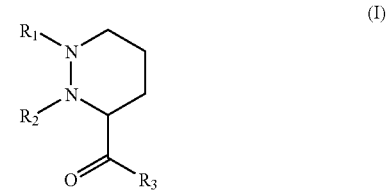

(I)

herein, pharmaceutical composition thereof, process for its preparation, and its pharmaceutical use.

19 Claims, No Drawings

PYRIDAZINE DERIVATIVE, PHARMACEUTICAL COMPOSITION THEREOF, ITS PHARMACEUTICAL USE, AND PROCESS FOR ITS PREPARATION

CROSS REFERENCE

This application is a Continuation of International Application PCT/FR03/00381, filed Feb. 7, 2003.

FIELD OF THE INVENTION

The invention relates to a pyridazine derivative, pharmaceutical composition thereof, process for its preparation, and its pharmaceutical use, especially as a cathepsin K inhibitors.

BACKGROUND OF THE INVENTION

Metabolic enzymes such as proteases or kinases are enzymes that are widely distributed in the animal kingdom. Non-exhaustive examples that may be mentioned, as bibliographic references for the proteases, include documents: "Methods in Enzymology XLII (1975)" and "Journal of Medicinal Chemistry" Vol. 43, No. 3 (D. Leung, G. Abbenante and D. P. Fairlie), and, for the kinases, include document: "Methods in Enzymology", Vol. 80 (1981) (Academic Press Inc.).

Among the proteases capable of selectively catalyzing the hydrolysis of polypeptide bonds, mention may be made of the four main classes: aspartic protease, serine protease, cysteine protease and metalloprotease.

Aspartic proteases that may especially be mentioned include HIV-1 protease, renin, plasmepsins and cathepsin D.

Serine proteases that may especially be mentioned include thrombin, factor Xa, elastase, tryptase, "convertase complement" and hepatitis C protease NS3.

Among the cysteine proteases, there are three structurally different groups, the papain and cathepsin group, the ICE group (caspases) and the picorna-viral group (similar to the serine proteases, in which the serine is replaced with a cysteine).

Thus, mention may be made especially of cathepsin K, cathepsin B, cathepsin L, cathepsin S, caspases, rhinovirus 3C protease and papains and calpains.

Metalloprotease is that may especially be mentioned include angiotensin conversion enzyme, neutral endopeptidase and a mixture of the two, matrix metalloprotease and also tumor necrosis factor-α-converting enzyme.

These kinases or proteases are involved in catabolization and inter- and intracellular communication processes: they play an important role in a large number of diseases in various fields, such as, especially, the cardiovascular field, oncology, the central nervous system, inflammation, osteoporosis, and also parasitic, fungal or viral infectious diseases. Consequently, these proteins are targets of great interest for pharmaceutical research.

SUMMARY OF THE INVENTION

A subject of the present invention is a compound of formula (I):

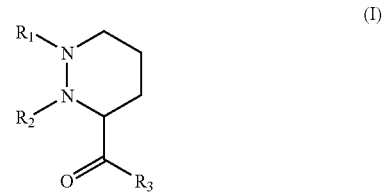

wherein $R_1$ is a hydrogen atom or a linear or branched alkyl group containing from 1 to 6 carbon atoms, COR or COOR, R being chosen from the group consisting of a linear or branched alkyl radical containing from 1 to 6 carbon atoms, optionally substituted with a pyridyl or carbamoyl radical, a linear or branched —$CH_2$-alkenyl radical containing in total from 3 to 9 carbon atoms, an aryl radical containing from 6 to 10 carbon atoms or an aralkyl radical containing from 7 to 11 carbon atoms, the nucleus of the aryl or aralkyl radical being optionally substituted with an OH radical, $NH_2$ radical, $NO_2$ radical, linear or branched alkyl radical containing from 1 to 6 carbon atoms or linear or branched alkoxy radical containing from 1 to 6 carbon atoms, or with 1 to 3 halogen atoms, $R_2$ is a group corresponding to formula (II) below:

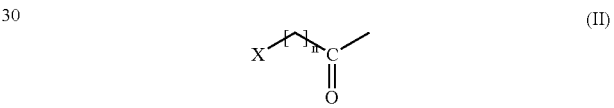

wherein n is 0, 1, 2 or 3; a double bond possibly being present when n is 2 or 3;

X is one of the following groups:

saturated or unsaturated monocyclic or bicyclic heterocyclic group;

an aryl group containing from 6 to 10 carbon atoms or an aralkyl group containing from 7 to 11 carbon atoms, the nucleus of the aryl or aralkyl radical being optionally substituted with an OH radical, $NH_2$ radical, $NO_2$ radical, linear or branched alkyl radical containing from 1 to 6 carbon atoms or linear or branched alkoxy radical containing from 1 to 6 carbon atoms, or with 1 to 3 halogen atoms;

a group $NR_4R_5$, $R_4$ being a linear or branched alkyl group containing from 1 to 6 carbon atoms or a group COR, CONHR, CSNHR or $SO_2R$, R having the meaning given above and $R_5$ being a hydrogen atom or a linear or branched alkyl radical containing from 1 to 6 carbon atoms; or a group COR, R having the meaning given above $R_3$ is group of formula —Y—$(CH2)_m$—$C(CN)R_6R_7$, wherein:

Y is an oxygen atom or a group —$N(R_8)$—, $R_8$ is a hydrogen atom or a linear or branched alkyl group containing from 1 to 6 carbon atoms, m is 0, 1, 2 or 3, $R_6$ is a hydrogen atom, a linear or branched alkyl group containing from 1 to 6 carbon atoms or an aryl or aralkyl group, the nucleus of the aryl or aralkyl radical being optionally substituted with an OH radical, $NH_2$ radical, $NO_2$ radical, linear or branched alkyl radical containing from 1 to 6 carbon atoms, linear or branched alkoxy radical containing from 1 to 6 carbon atoms, or aryloxy radical of 7 to 11 carbon atoms, this aryloxy group being itself optionally substituted with 1 to 3 halogen atoms; and $R_7$ is hydrogen atom or a linear or branched alkyl group containing from 1 to 6 carbon atoms, or $R_6$ and $R_7$ taken together with the carbon to which they are attached form cyclohexyl, or the compound of formula (I) being in any possible racemic, enantiomeric or diastereoisomeric form; or an addition salt of the compound of formula (I) with a mineral and organic acid or with mineral and organic base.

The invention also relates to a pharmaceutical composition of the pyridazine derivative, process for its preparation, and its pharmaceutical use, especially as a cathepsin K inhibitors.

DETAILED DESCRIPTION OF THE INVENTION

Definition of Terms

As used above, and throughout the description of the invention, the following terms, unless otherwise indicated, shall be understood to have the following meanings.

the term "aryl containing from 6 to 10 carbon atoms" denotes an unsaturated radical comprising one or two fused rings, optionally interrupted with one to three hetero atoms is chosen from nitrogen, oxygen and sulfur. Mention may be made of: phenyl, naphthyl;

the term "aralkyl containing from 7 to 11 carbon atoms" denotes an aryl radical as defined above, linked via a linear or branched alkyl radical, this alkyl radical containing from 1 to 5 carbon atoms. Mention may be made especially of benzyl;

the term "aralkyloxy" indicates the presence of a terminal oxygen on the abovementioned aralkyl group;

the term "monocyclic heterocyclic radical" denotes a saturated or unsaturated, 5- or 6-membered ring such that one or more of the members is an oxygen, sulfur or nitrogen atom: such a heterocyclic radical thus denotes a carbocyclic radical interrupted with one or more hetero atoms chosen from oxygen, nitrogen and sulfur atoms, it being understood that the heterocyclic radicals may contain one or more hetero atoms chosen from oxygen, nitrogen and sulfur atoms, and that, when these heterocyclic radicals comprise more than one hetero atom, the hetero atoms of these heterocyclic radicals may identical or different. Mention may be made especially of dioxolane, dioxane, dithiolane, thioxolane, thioxane, morpholinyl, piperazinyl, piperazinyl substituted with a linear or branched alkyl radical containing up to 4 carbon atoms, piperidyl, thienyl such as 2-thienyl and 3-thienyl, furyl such as 2-furyl, pyrimidyl, pyridyl such as 2-pyridyl, 3-pyridyl and 4-pyridyl, pyrimidyl, pyrrolyl, thiazolyl, isothiazolyl, diazolyl, thiadiazolyl, triazolyl, free or salified tetrazolyl, thiadiazolyl, thiatriazolyl, oxazolyl, oxadiazolyl, and 3- or 4-isoxazolyl radicals. Mention may be made most particularly of morpholinyl, thienyl such as 2-thienyl and 3-thienyl, furyl such as 2-furyl, tetrahydrofuryl, thienyl, tetrahydrothienyl, pyrrolyl, pyrrolinyl, pyridyl and pyrrolidinyl radicals. A particular a monocyclic heterocyclic radical is an 6-membered aza-heterocyclyl wherein the aza prefix denotes that one member of the group is a nitrogen atom;

the term "bicyclic heterocyclic radical" denotes a saturated or unsaturated 8- to 12-membered radical such that one or more of the members is an oxygen, sulfur or nitrogen atom, and especially fused heterocyclic groups containing at least one hetero atoms chosen from sulfur, nitrogen and oxygen, for example benzothienyl such as 3-benzothienyl, benzothiazolyl, quinolyl, tetralone, benzofuryl, benzopyrrolyl, benzimidazolyl, benzoxazolyl, thionaphthyl, indolyl or purinyl.

The compounds of formula (I) may be salified with various groups known to those skilled in the art, among which examples that may be mentioned include:

among the salified compound of formula (I), include those with mineral bases, for instance one equivalent of sodium hydroxide, potassium hydroxide, lithium hydroxide, calcium hydroxide, magnesium hydroxide or ammonium hydroxide, or organic bases, for instance methylamine, propylamine, trimethylamine, diethylamine, triethylamine, N,N-dimethylethanolamine, tris-(hydroxymethyl)aminomethane, ethanolamine, pyridine, picoline, dicyclohexylamine, morpholine, benzylamine, procaine, lysine, arginine, histidine, and N-methylglucamine, the addition salts of the compound of formula (I) with mineral or organic acids may be, for example, the salts formed with hydrochloric acid, hydrobromic acid, hydriodic acid, nitric acid, sulfuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids, for instance methane-sulfonic acid, ethanesulfonic acid, propane-sulfonic acid, alkyldisulfonic acids, for instance methanedisulfonic acid and $\alpha,\beta$-ethanedisulfonic acid, arylmonosulfonic acids, for instance benzenesulfonic acid, and aryldisulfonic acids.

Stereoisomerism is defined in its broadest sense as being the isomerism of compounds having the same structural formula, but whose various groups are arranged differently in space, especially such as in monosubstituted cyclohexanes in which the substituent may be in an axial or equatorial position, and the various possible rotational conformations of the ethane derivatives. However, there is another type of stereoisomerism, caused by the different spatial arrangements of attached substituents, either on double bonds or on rings, which is often referred to as geometrical isomerism or cis-trans isomerism. The term "stereoisomers" is used herein in its broadest sense and thus covers all the compounds indicated above.

Embodiments

A subject of the present invention is especially the compound of formula (I) as defined above, in which $R_1$ is a hydrogen atom or a methyl, benzyl, —COO-benzyl or —CO-methylenebenzyl group, in particular those in which n is equal to 0 or 2.

Another embodiment of the invention is the compound of formula (I) wherein $R_5$ is hydrogen atom.

Another embodiment of the invention is the compound of formula (I) wherein X is a phenyl or —NHCO-benzyl group or those in which X is a group

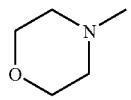

Another embodiment of the invention is the compound of formula (I) wherein $R_6$, $R_7$ and/or $R_8$ are, independently of each other, a hydrogen atom.

Another embodiment of the invention is the compound of formula (I) wherein $R_6$ is a phenyl, —$C_6H_4$—O—$C_6H_5$ or —$C_2H_4$—O—$C_6H_4Br$ group.

Another embodiment of the invention is the compound of formula (I) wherein m is equal to 0 or 2.

Another embodiment of the invention are certain species of the compound of formula (I).

Processes According to the Invention

Another aspect of the present invention is also a process for preparing the compound of formula (I) as defined above, wherein it includes a step of reaction of a compound of formula (IV)

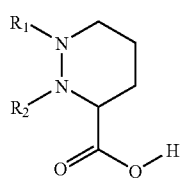
(IV)

in which $R_1$ and $R_2$ have the same meaning as above, with an aminonitrile or cyanohydrin of formula $HR_3$, in which $R_3$ has the same meaning as above, to obtain a compound of formula (I).

Another aspect of the present invention is thus also a process for preparing the compound of formula (I) as defined above, wherein it includes:

1) a step during which a compound of formula (II)

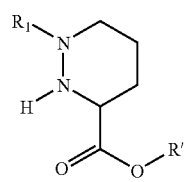
(II)

is reacted with an acid chloride of formula $R_2Cl$, in which $R_1$ and $R_2$ have the same meanings as above and R' is a linear or branched alkyl group containing from 1 to 6 carbon atoms, to obtain the compound of formula (III):

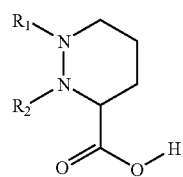

2) a step during which the compound of formula (III) obtained in step 1) is hydrolyzed to the compound of formula (IV):

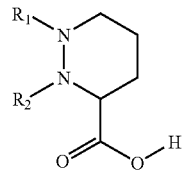

3) a step during which the compound of formula (IV) obtained in step 2) is reacted with an aminonitrile or cyanohydrin of formula $HR_3$, in which $R_3$ has the same meaning as above, to obtain a compound of formula (I).

The starting material of the first process described is a pyridazinecarboxylic acid of formula (IV), which is reacted directly with a suitable nitrile derivative.

The second process is based on the preparation of an intermediate ester.

Such a process thus consists essentially of the following three steps:

step 1) allows the compound of formula (III)

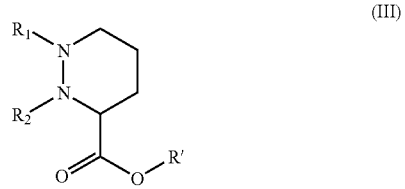
(III)

to be obtained from the compound of formula (II);

step 2), which is a step that is known per se of hydrolysis of an ester and generally takes place in the presence of a base, allows the compound of formula (IV)

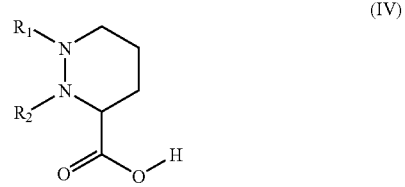
(IV)

to be obtained from the starting material of formula (III);

step 3) allows the compound of formula (I) to be obtained from the compound of formula (IV).

As regards the additional steps, they are in general standard reactions that are well known to those skilled in the art.

Thus, the reactive functions that are suitable to protect, where appropriate, are generally carboxylic acid, amine, amide and hydroxyl functions.

The protection of the acid function is especially performed in the form of alkyl esters, or allylic, benzyl, benzhydryl or p-nitrobenzyl esters.

The deprotection is performed by saponification, acid hydrolysis, hydrogenolysis or cleavage using soluble palladium 0 complexes.

The protection of the amines and amides is especially performed in the form of benzyl derivatives, in the form of carbamates, especially allyl, benzyl, phenyl or tert-butyl carbamates, or alternatively in the form of silyl derivatives such as tert-butyldimethylsilyl, trimethyl-, triphenyl- or diphenyl-tert-butylsilyl derivatives.

The deprotection is performed, depending on the nature of the protecting group, with sodium or lithium in liquid ammonia, by hydrogenolysis or using soluble palladium 0 complexes, via the action of an acid or via the action of tetrabutylammonium fluoride.

The protection of the alcohols is conventionally performed in the form of ethers, esters or carbonates. The ethers may be alkyl or alkoxyalkyl ethers, preferably methyl or methoxyethoxymethyl ethers, aryl and preferably aralkyl ethers, for example benzyl ethers, or silyl ethers, for example the silyl derivatives mentioned above. The esters may be any cleavable ester known to those skilled in the art, and preferably acetate, propionate, benzoate or p-nitrobenzoate. The carbonates may be, for example, methyl, tert-butyl, allyl, benzyl or p-nitrobenzyl carbonate.

The deprotection is performed by the means known to those skilled in the art, especially saponification, hydrogenolysis, cleavage with soluble palladium 0 complexes, hydrolysis in acidic medium or alternatively, for the silyl derivatives, treatment with tetrabutylammonium fluoride.

The amidation reaction is performed starting with the carboxylic acid, using an activating agent such as an alkyl chloroformate or EDCI, via the action of aqueous ammonia or a suitable amine, or the acid salts thereof.

The acylation and sulfonylation reactions are performed on the hydroxy ureas via the action, respectively, of a suitable carboxylic acid halide or anhydride or a suitable sulfonyl halide.

The alkylation reaction is performed via the action on the hydroxy derivatives of an alkyl or substituted alkyl halide, especially a free or esterified carboxyl radical.

The optional final introduction of a double bond is performed via the action of a halogenated selenium derivative followed by oxidation, according to methods known to those skilled in the art.

The formation of a urea group is preferably performed via the action of a suitable isocyanate on the free NH.

The reduction of acids to alcohols may be performed via the action of a borane or via an intermediate mixed anhydride, via the action of an alkali metal borohydride. The mixed anhydride is prepared, for example, using an alkyl chloroformate.

The dehydration of amide to nitrile may take place under the conditions of the carbonylation and cyclization reactions.

The salification with acids is performed, where appropriate, by addition of an acid in soluble phase to the compound. The salification with bases may concern either compounds comprising an acid function, especially carboxyl, or those comprising a sulfoxy function or those comprising a heterocycle of acidic nature. In the first case, the process is performed by adding a suitable base such as those mentioned above.

In the second case, the pyridinium salt is obtained directly during the action of the $SO_3$-pyridine complex, and the other salts are obtained from this pyridinium salt. In either case, the process may still be performed by ion exchange on a resin. Examples of salifications are given hereinbelow in the experimental section.

The separation of the enantiomers and diastereoisomers may be performed according to the techniques known to those skilled in the art, especially chromatography.

The final step of the process according to the invention may be followed, where appropriate, by a hydrogenolysis so as to convert the group $R_1$ into a hydrogen atom.

The process for preparing a compound of formula (I) includes one or more of the following optional reactions, undertaken in an appropriate order:
protection of reactive functions;
deprotection of reactive functions;
esterification;
saponification;
amidation;
acylation;
sulfonylation;
alkylation;
introduction of a double bond;
formation of a urea group;
reduction of carboxylic acids;
dehydration of amide to nitrile;
salification;
ion exchange;
resolution or separation of diastereoisomers.

Illustrations of such reactions defined above are given in the examples described below.

Utility of the Compound of the Formula (I)

The compound of formula (I) as defined above, and the addition salts thereof with acids, have advantageous pharmacological properties.

The compound of formula (I) has inhibitory properties on one or more metabolic enzymes as defined above, especially kinases or proteases.

The compound of formula (I) of the present invention as defined above has inhibitory properties on certain protein kinases or proteases, more especially cysteine proteases or serine proteases.

Further more the compound of formula (I) is useful in preventing or treating diseases in which such metabolic enzymes are involved, for instance certain cardiovascular diseases, diseases of the central nervous system, inflammatory diseases, bone diseases, for instance osteoporosis, infectious diseases especially requiring anti-infectious agents for their treatment, or certain cancers.

Protein kinases of interest, include cathepsins B, H, J, L, N, S, T, C, V, W, K or O, and O2; especially those involved in the bone and cartilage metabolism diseases and bone cancers, and most particularly cathepsin K.

The levels, regulation and activity of a certain number of protein kinases or proteases play a role in several human pathologies. The activity of a protein kinase or protease may especially be associated with receptors having transmembrane domains or with intracellular proteins.

Certain kinases or proteases may play a role in the initiation, development and completion of cell cycle events, and thus, molecules that inhibit such kinases or proteases are liable to limit undesired cell proliferations such as those observed in cancers, psoriasis, growth of fungi and parasites (animals, protists): such molecules that inhibit these kinases or proteases are thus liable to intervene in the regulation of neurodegenerative diseases such as Alzheimer's disease.

The compound of formula (I) of the present invention has antimitotic properties.

The compound of formula (I) as defined above may, as kinase or protease inhibitors, especially have the property of inhibiting osteoclast-mediated bone resorption. They are useful for the therapeutic or prophylactic treatment of diseases that are at least partially caused by an undesired increase in bone resorption, for example osteoporosis.

The compound of formula (I) of the present invention is thus, for example, an inhibitor of the adhesion of osteoclasts on the surface of bone and thus bone resorption by the osteoclasts.

The bone diseases whose treatment or prevention require the use of the compound of formula (I) are especially osteoporosis, hypercalcaemia, osteopenia, for example caused by bone metastases, dental disorders, for example periodontitis, hyperparathyroidism, periarticular erosions in rheumatoid arthritis, Paget's disease, osteopenia induced by immobilization. In addition, the compound of formula (I) is used to ease, prevent or treat bone disorders that are caused by the treatments or by glucocorticoids, therapies associated with the taking of steroids or corticosteroids, or by with male or female sex hormone deficiencies.

All these disorders are characterized by bone loss, which is based on an equilibrium defect between bone formation and bone destruction and which is favorably influenced by inhibiting the bone resorption by the osteoclasts.

The compound of formula (I) of the present invention is, in addition to its specific inhibitory properties on kinases or proteases, has advantageous cellular effects such as antiproliferative properties and especially effects on apoptosis.

It is known from studies described in the literature, such as in WO 97/20842, that relationships exist between the cell cycle and apoptosis. Among the pathways leading to apoptosis, certain are dependent on kinases or proteases.

The products of the present invention are especially useful for tumor therapy.

The products of the invention also increase the therapeutic effects of commonly used antitumor agents.

The compound of formula (I) of the present invention also has antimitotic and anti-neurodegenerative properties.

The compound of formula (I) is also an inhibitor of vasoconstrictive and hypertensive effects and thus produces an anti-ischemic effect, or counter stimulatory effects on certain cell types, especially smooth muscle cells, fibroblasts, neurons and bone cells.

The compound of formula (I) is thus be used in the treatment of diseases such as proliferative diseases, cancer, restenosis, inflammation; allergies, cardiovascular diseases or certain infectious diseases.

The compound of formula (I) is also be used in the treatment of certain gastrointestinal and gynecological disorders and in particular for a relaxing effect on the uterus.

The noted utilities herein are another aspect of the invention.

Pharmaceutical Compositions

Another aspect of the invention is, are pharmaceutical compositions containing, as active principle, at least one species of the compound according to the invention in a pharmaceutically effective amount, in combination with a pharmaceutically acceptable support.

The pharmaceutical compositions of the present invention as defined above may be administered orally, parenterally or locally by topical application to the skin and mucous membranes or by intravenous or intramuscular injection.

These compositions may be solid or liquid and may be in any pharmaceutical form commonly used in human medicine, for instance plain or sugar-coated tablets, pills, lozenges, gel capsules, drops, granules, injectable preparations, ointments, creams or gels; they are prepared according to the usual methods. The active principle may be incorporated therein with excipients usually used in these pharmaceutical compositions, such as talc, gum arabic, lactose, starch, magnesium stearate, cocoa butter, aqueous or nonaqueous vehicles, fatty substances of animal or plant origin, paraffinic derivatives, glycols, various wetting agents, dispersants or emulsifiers, and preserving agents.

The usual dosage, which may vary according to the product used, the individual treated and the complaint under consideration, may be, for example, from 0.05 to 5 g per day and preferably from 0.1 to 2 g per day per day in adults.

EXPERIMENTAL

The species of the compound of formula (I) in the following examples are characterized by their NMR spectra (300 Hz in $CDCl_3$ or DMSO) and by their molecular mass MM (electrospray in positive mode; results in the form of the mass of the molecular ion $H^+$ or in the form of a sodium adduct).

The starting compound of formula (II) is known or may be prepared according to methods known to those skilled in the art. Literature references and preparations are optionally given hereinbelow in the experimental section.

The examples that follow illustrate the invention without, however, limiting its scope.

In the examples that follow, the following abbreviations have been used:

M: molecular molar mass
MS: mass spectrometry
EDCI: 1-(3-dimethylaminopropyl)-3-ethylcarbodiimide hydrochloride
EtOAc: ethyl acetate
DMF: N,N-dimethylformamide
HOBt: 1-hydroxybenzotriazole hydrate
DMSO: dimethyl sulfoxide Example 1

Synthesis of an Acid $R_2OH$ 10.69 g (0.12 mM) of β-alanine are dissolved in 60 ml of 2N NaOH (0.12 mM). 17.6 μl (0.132 mM) of benzyl-methanoic acid chloride and 66 ml (0.132 mM) of 2N NaOH are added dropwise.

The mixture is stirred for 1 hour 30 minutes at 0° C. The reaction medium is extracted twice with 25 ml of diethyl ether and then brought to pH 3 with 65 ml of 2N HCl solution. The precipitate formed is filtered off and dried. 23.4 g of a white solid corresponding to 3-[(phenylacetyl)amino]propanoic acid are recovered.

The corresponding yield is 94.2%. Proton NMR spectrum In DMSO, at 300 MHz, chemical shifts of the peaks in ppm and multiplicity: 2.5 (t, $2H_a$); 3.35 (q, $2H_b$); 3.5 (s, $1H_c$); 7.3 to 7.5 (m, 5H); 8.25 (t, 1H)

Example 2

Synthesis of an Intermediate Acid

Step A 291 mg (1.4 mM) of the acid obtained in example 1 are dissolved in 5 ml of dichloromethane and 0.5 ml of DMF, and 368 ml (4.21 mM) of oxalyl chloride are added dropwise.

After stirring at room temperature for 3 hours, the acid chloride is formed and is used without further purification for the rest of the synthesis.

390 mg (1.4 mM) of pyridazine derivative dissolved in 5 ml of dichloromethane and 733 ml of DMF are added to the above solution, said pyridazine derivative corresponding to 1-(phenylmethyl)-3-methyl (3S)-tetra-hydro-1,3(2H)-pyridazinedicarboxylate. This compound is obtained by esterification of the corresponding pyridazine-3-carboxylic acid (see also the description as an intermediate product in documents WO-A-99/55724, WO-A-97/22619 and EP-A-25941).

The reaction medium is stirred at room temperature for 12 hours.

The resulting mixture is concentrated and purified by flash chromatography with an 80/20 ethyl acetate/dichloromethane mixture. 150 mg of the expected product, corresponding to 1-(phenylmethyl)-3-methyl (3S)-2-[1-oxo-3-[(phenylacetyl)amino]propyl]hexahydro-1,3(2H)-pyridazinedicarboxylate, are recovered.

The corresponding yield is 26%. Proton NMR Spectrum In CDCl$_3$, at 300 MHz, chemical shifts of the peaks in ppm and multiplicity: 1.46 and 2.04 (m, 2H$_e$); 1.72 and 2.1 (m, 2H$_d$), 2.61 (m, 2H$_b$); 2.90 m, 4.04 and 4.14 (broad d, 2H$_f$), 3.47 (m, 2H$_a$); 3.48 (m, 2H$_h$); 3.54 (broad s, 3H); 4.73 to 4.98 (m, 1H$_g$); 5.18 (broad s, 1H$_c$); 5.22 (broad s, 1H$_g$), 5.96 and 6.07 (d, 1H); 7 to 7.4 (m, 10H).

Step B 38 mg (0.08 mM) of the ester obtained in step A are dissolved in 2 ml of methanol. 8.3 µl (0.16 mM) of 2N sodium hydroxide solution are added. The reagents are left in contact for 4 hours at room temperature. The reaction medium is concentrated, extracted with 25 ml of ethyl acetate and then acidified with 1N HCl solution to pH 1 and then extracted with 25 ml of ethyl acetate solution. The organic solution is dried and concentrated to give 31 mg of oil corresponding to the desired carboxylic acid derivative.

The corresponding yield is 84%. Proton NMR Spectrum In CDCl$_3$, at 300 MHz, chemical shifts of the peaks in ppm and multiplicity: 1.46 and 1.75 (m, 2H$_e$); 1.67 and 2.31 (m, 2H$_d$), 2.47 (m, 2H$_b$); 2.90 m, 4.04 and 4.14 (broad d, 2H$_f$), 3.47 (m, 2H$_a$); 3.48 (m, 2H$_h$); 4.73 to 4.98 (m, 1H$_g$); 5.18 (broad s, 1H$_c$); 5.22 (broad s, 1H$_g$), 5.96 and 6.07 (d, 1H); 7 to 7.4 (m, 10H).

Example 3

Synthesis of an Aminonitrile HR$_3$ 9.59 g (29.8 mM) of a 70% solution in ether of 3-phenoxybenzaldehyde cyanohydrin are dissolved in 60 ml of ethanol in a 100 ml metallic bomb in the presence of 10 g of MgSO$_4$.

Ammonia gas is bubbled therein for 1 hour, while keeping the medium at −10° C., and stirring of this mixture is continued at room temperature for 18 hours. The mixture is then filtered and evaporated to dryness.

The residue is taken up in 50 ml of an aqueous pH 1 solution and extracted with 50 ml of ethyl acetate. The aqueous phase is then neutralized with Na$_2$CO$_3$ and then extracted twice with 50 ml of ethyl acetate. 100 ml of 20% HCl/EtOAc solution are added to this solution. The final solution is concentrated to give 3.12 g of a beige powder corresponding to 3-phenoxy-α-aminobenzene-acetonitrile.

The corresponding yield is 40%. Proton NMR Spectrum In CDCl$_3$, at 300 MHz, chemical shifts of the peaks in ppm and multiplicity: 4.88 (broad s, 1H); 7.0 (s, 1H$_d$); 7.02 (dd, 2H$_g$); 7.14 (broad t, 1H$_e$); 7.19 (1H, H$_a$); 7.26 (broad d, 1H$_b$); 7.36 (m, 2H$_f$); 7.37 (m, 1H).

Example 4

31 mg of the acid obtained in example 2 are dissolved in 1 ml of DMF. 14 mg (0.1 mM) de HOBT (1-hydroxybenzotriazole) and then 20 mg (0.1 mM) of EDCI are added to the medium cooled to 0° C. (ice-salt bath) The mixture is warmed to room temperature and stirred for 1 hour. 15.3 mg (0.068 mM) of the amine obtained in example 3 dissolved in 2 ml of DMF and 36 µl (0.2 mM) of DIPEA (diisopropylethylamine) are then added to the reaction medium. The mixture is kept at room temperature for 12 hours and then poured into 25 ml of water. The solution is extracted with 25 ml of EtOAc, dried and concentrated. The residue obtained is purified by flash chromatography. 22 mg of the expected product, corresponding to (phenylmethyl) (3S)-2-[1-oxo-3-[(phenylacetyl)amino]propyl]-3-[[[cyano(3-phenoxy-phenyl)methyl]amino]carbonyl]tetrahydro-1(2H)pyridazine-carboxylate, are recovered.

The corresponding yield is 50%. Proton NMR Spectrum In CDCl$_3$, at 300 MHz, chemical shifts of the peaks in ppm and multiplicity: 1.46 to 1.75 (m, 2H$_e$); 1.67 and 2.31 (m, 2H$_d$); 2.47 (m, 2H$_b$); 2.9 (m, 1H$_f$); 3.47 (m, 2H$_a$); 3.48 (m, 2H$_h$); 4.04 and 4.14 (broad d, 1H$_f$); 4.73, 4.98 and 5.22 (m, 2H$_g$); 5.18 (broad s, 1H$_c$); 6.07 (m, 1H); 5.96 and 6.03 (d, 1H$_c$); 6.07 (m, 1H); 6.9 to 7.47 (m, 19H$_{Ar}$); 8.42 and 8.5 (broad d, 1H).

Example 5

19 mg (0.029 mM) of the 50/50 mixture obtained in example 4 are dissolved in 2 ml of ethanol. 10 mg of 10% Pd/C are added to this solution. The mixture is stirred for 15 hours at room temperature. The reaction medium is filtered and then concentrated. The residue obtained is purified by flash chromatography to give 10 mg of the expected product as a 50/50 mixture of 2 diastereoisomers, (S,S) and (S,R), corresponding to (3S)-2-[3-[(phenylacetyl)amino]-1-oxo-propyl]-N-[cyano-(3-phenoxyphenyl)methyl]hexahydro-3-pyridazine-carboxamide.

The corresponding yield is 67%. Proton NMR Spectrum In CDCl$_3$, at 300 MHz, chemical shifts of the peaks in ppm and multiplicity: (50/50 mixture of the 2 diastereoisomers): 1.58 (m, 2H$_e$); 1.70 and 2.37 (m, 2H$_d$); 2.33 and 2.94 (m, 2H$_b$); 2.68, 2.72, 2.91 and 3.01 (m, 2H$_f$); 3.27 and 3.37 (m, 1H$_h$); 3.52 (broad s, 1H$_h$); 3.83 (broad s), 3.96 (broad s) and 3.16 (broad d, 2H$_a$); 5.14 (broad s, 1H$_c$); 5.89 and 5.97 (broad s, 1H); 6.09 and 6.18 (d, 1H$_i$); 8.24 and 8.49 (broad d, 1H).

Example 6

Starting with the mixture obtained in example 4, the two pure diastereoisomers are separated and then hydrogenated separately, under the same conditions as for example 5.

Two pure separate diastereoisomers are thus obtained (the formula of which is obviously the same as that given in example 5).

Example 7

The process is performed as in example 4, except that, instead of using the amine obtained in example 3, 3-phenoxybenzaldehyde cyanohydrin (starting material used to prepare this amine) is used directly.

A mixture of diastereoisomers corresponding to 1-(phenylmethyl)-3-[(R)-cyano(3-phenoxyphenyl)methyl](3S)-2-[1-oxo-3-[(phenylacetyl)amino]propyl]tetrahydro-1,3(2H)-pyridazinedicarboxylate is thus obtained.

Proton NMR Spectrum In DMSO, at 300 MHz, chemical shifts of the peaks in ppm and multiplicity: 1.49 and 1.79 (m, 2H); 1.80 and 1.90 (m, 2H); 2.30 and 2.54 (m, 2H); 3.01 and 4.09 (m, 2H); 3.36 (broad s, 2H); 3.27 (m, 2H); 4.89 and 5.11 (m, 1H); 4.98 and 5.15 (m, 1H); 5.31 (broad s, 1H); 6.49 and 6.59 (broad s, 1H); 6.90 to 7.50 (m, 19H).

Example 8

The compound obtained in example 7 is deprotected by hydrogenation as indicated in example 5. A mixture of two diastereoisomers corresponding to 3-[cyano(3-phenoxyphenyl)methyl] (3S)-2-[1-oxo-3-[(phenylacetyl)-amino]propyl] tetrahydro-1,3-(2H)-pyridazinecarboxylate is thus obtained.

Example 9

The process is performed as in example 4, except that instead of using the amine obtained in example 3, commercial 3-(p-bromophenoxy)benzaldehyde cyanohydrin is used.

A 50/50 mixture of 2 diastereoisomers corresponding to 1-(phenylmethyl)-3-[cyano-3-[(4-bromophenoxy)phenyl]-methyl] (3S)2-[1-oxo-3-[(phenylacetyl)amino]propyl]-tetrahydro-1,3(2H)-pyridazinedicarboxylate is thus obtained.

Proton NMR Spectrum In DMSO, at 300 MHz, chemical shifts of the peaks in ppm and multiplicity: 1.51 and 1.78 (m, $2H_e$); 1.76 and 1.97 (m, $2H_d$); 2.24 and 2.54 (m, $2H_b$); 3.22 (m, $2H_b$); 3.35 (m, $2H_h$); 4.03 (m, $2H_f$); 5.12 (broad s, $1H_g$); 5.18 (broad s, $1H_g$); 5.36 (m, $1H_c$); 6.61 (m, $1H_i$); 7.01 to 7.57 (m, $18H_{Ar}$).

MS (Negative electrospray) m/z: $[M]^-$=737

Example 10

The process is performed as in example 4, except that instead of using the amine obtained in example 3, commercial (cyanoaminomethyl)benzene is used.

A compound corresponding to (phenylmethyl) (3S)-3-[[(cyanophenylmethyl)amino]carbonyl]-2-[1-oxo-3-[(phenylacetyl)amino]propyl]tetrahydro-1(2H)-pyridazinecarboxylate is thus obtained.

MS (Positive electrospray) m/z: $[MH]^+$=568.3 $[MNa]^+$=590.2

Example 11

The compound obtained in example 10 is deprotected by hydrogenation as indicated in example 5.

The compound corresponding to (3S)-N-(cyanophenylmethyl)-2-[1-oxo-3-[(phenylacetyl)amino]propyl]hexa-hydro-3-pyridazinecarboxamide is obtained.

Proton NMR Spectrum In CDCl$_3$, at 300 MHz, chemical shifts of the peaks in ppm and multiplicity: 1.58 (m, 2H); 1.71 (m, 1H); 2.35 (m, 1H); 2.28 and 2.98 (m, 1H); 2.38 and 2.87 (m, 1H); 2.70 and 2.97 (m, 2H); 3.16 and 3.92 (m, 1H); 3.19 and 3.77 (m, 1H); 3.54 (broad s, 2H); 5.14 (broad s, 1H); 5.89 and 6.02 (broad s, 2H); 6.09 and 6.21 (broad d, 1H); 7.12 to 7.56 (m, 10H); 8.09 and 8.44 (broad d, 1H).

Example 12

The process is performed as in example 4, except that instead of using the amine obtained in example 3, commercial cyanoaminomethane is used.

A compound corresponding to (phenylmethyl) (3S)2-[1-oxo-3-[(phenylacetyl)amino]propyl]-3-[[(cyanoamino)-carbonyl]tetrahydro-1(2H)-pyridazinecarboxylate is thus obtained.

MS (Positive electrospray) m/z:$[MH]^+$=492.3 $[MNa]^+$=514.3

Example 13

The compound obtained in example 10 is deprotected by hydrogenated as indicated in example 5.

The compound corresponding to (3S)-N-cyano-2-[1-oxo-3-[(phenylacetyl)amino]propyl]hexahydro-3-pyridazinecarb-oxamide is obtained.

Proton NMR Spectrum In CDCl$_3$, at 300 MHz, chemical shifts of the peaks in ppm and multiplicity: 1.56 (m, 2H); 1.66 and 2.46 (m, 2H); 2.26 and 3.10 (m, 2H); 2.72 and 2.99 (m, 2H); 3.20 and 4.08 (m, 2H); 3.55 (broad s, 2H); 3.78 and 4.09 (dd, 2H); 5.12 (broad d, 1H); 6.04 (m, 1H); 7.19 to 7.40 (m, 5H); 7.97 (broad t, 1H)

Example 14

Step A

The process is performed as indicated in step A of example 2, except that instead of using the acid R$_2$OH obtained in example 1,3-phenylpropanoic acid is used. A compound corresponding to (phenylmethyl) (3S)-3-acetyl-2-[3-phenyl-1-oxopropyl]tetrahydro-1(2H)-pyridazinecarboxylate is thus obtained.

Proton NMR Spectrum In CDCl$_3$, at 300 MHz, chemical shifts of the peaks in ppm and multiplicity: 1.46 and 2.04 (m, 2H); 1.72 and 2.04 (m, 2H); 2.60 and 4.21 (m, 2H); 2.61 and 2.91 (m, 4H); 3.54 (broad s, 3H); 5.05 and 5.25 (d, 2H); 5.41 (broad d, 1H); 7.10 to 7.33 (m, 10H)

Step B

The product obtained in step A as indicated in step B of example 2 is saponified to obtain an acid.

Proton NMR Spectrum In CDCl$_3$, at 300 MHz, chemical shifts of the peaks in ppm and multiplicity: 1.5 (m, 2H); 1.90 (m, 2H); 2.6 (m, 2H); 3.0 (m, 2H); 4.1 (m, 1H); 5.3 (m, 2H); 7.35 (m, 5H); 7.4 (m, 5H).

Step C

The coupling is performed as indicated in example 4.

A compound corresponding to (phenylmethyl) (3S)-3-[[[cyano(3-phenoxyphenyl)methyl]amino]carbonyl]-2-[3-phenyl-1-oxopropyl]tetrahydro-1(2H)-pyridazine-carboxylate is thus obtained.

MS (Positive electrospray) m/z: $[MH]^+$=740.7

Example 15

The compound obtained in example 14 is deprotected by hydrogenation as indicated in example 5.

Two diastereoisomers corresponding to (3S)-N-[cyano(3-phenoxyphenyl)methyl]-2-(1-oxo-3-phenylpropyl)hexa-hydro-3-pyridazinecarboxamide are thus obtained.

Proton NMR spectrum of one of the diastereoisomers In CDCl$_3$, at 300 MHz, chemical shifts of the peaks in ppm and multiplicity: 1.52 and 1.71 (m, 2H); 1.77 and 2.09 (m, 2H);

2.62 and 3.02 (m, 2H); 2.87 and 2.90 (m, 4H); 5.18 (broad s, 1H); 6.03 (broad s, 1H); 6.93 to 7.43 (m, 14H). Proton NMR Spectrum of the Other Diastereoisomer In CDCl$_3$, at 300 MHz, chemical shifts of the peaks in ppm and multiplicity: 1.51 and 1.75 (m, 2H); 1.78 and 2.06 (m, 2H); 2.57 and 2.98 (m, 2H); 2.74 and 2.79 (m, 4H); 5.27 (broad s, 1H); 5.96 (broad s, 1H); 6.91 to 7.38 (m, 14H).

Example 16

Step A 1 g (3.6 mmol) of the pyrazine derivative used in example 2 is dissolved in 20 ml of dichloromethane. 0.465 g (3.6 mmol) of DIPEA and 0.616 g (3.6 mMol) of 3-bromopropanoyl chloride are added to the solution. The mixture is stirred for 12 hours at room temperature. The reaction medium is concentrated to dryness, taken up in 25 ml of ethyl acetate and washed with 25 ml of 1N HCl solution. The organic phase is dried. The oil obtained is purified by flash chromatography. 1.1 g of the expected product corresponding to 1-(phenylmethyl)-3-methyl (3S)-2-(3-bromo-1-oxopropyl)tetrahydro-1,3(2H)-pyridazinedicarboxylate are obtained.

The corresponding yield is 75%. Proton NMR Spectrum In CDCl$_3$, at 300 MHz, chemical shifts of the peaks in ppm and multiplicity: 1.99 and 2.07 (m, 2H); 1.83 and 2.09 (m, 2H), 2.94 (m, 2H); 3.48 and 3.61 (m, 2H); 3.03 and 4.33 (m, 2H); 3.56 (broad s, 3H); 5.09 and 5.27 (m, 2H); 5.40 (dd, 1H); 7.39 (m, 5H)

Step B 0.2 g (0.48 mmol) of the compound obtained in the preceding step is dissolved in 2 ml of DMF. 0.421 mg (4.8 mmol) of morpholine is added to the solution. The mixture is stirred for 16 hours. The medium is poured into 25 ml of water and then extracted with 25 ml of ethyl acetate.

The organic phase is dried and concentrated. The residue obtained is purified by flash chromatography. 91 mg of the expected product are obtained.

The corresponding yield is 50%. Proton NMR Spectrum In CDCl$_3$, at 300 MHz, chemical shifts of the peaks in ppm and multiplicity: 1.53 and 1.92 (m, 2H); 1.78 and 1.92 (m, 2H); 2.3 to 2.7 (m, 4H); 3.52 (s, 3H); 3.38 (m, 4H); 3.57 (m, 4H); 5.18 (m, 1H); 5.04 and 5.2 (m, 2H); 7.35 (m, 4H).

Step C

The product obtained in step B is saponified as indicated in step B of example 2.

Proton NMR Spectrum In DMSO, at 300 MHz, chemical shifts of the peaks in ppm and multiplicity: 1.43 (m, 2H); 1.30 and 1.97 (m, 2H); 2.16 (m, 4H); 2.82 and 4.07 (m, 2H); 3.43 (m, 4H); 4.40 (m, 4H); 4.66 (d, 1H); 4.85 and 5.16 (d, 2H); 7.30 (m, 5H).

Step D

The process is performed as in example 4, except that instead of using the amine obtained in example 3, commercial (cyanoaminomethyl)benzene is used.

A 50/50 mixture of two diastereoisomers corresponding to (phenylmethyl) (3S)-3-[[(cyanophenylmethyl)amino]-carbonyl]-2-(4-morpholinylcarbonyl)tetrahydro-1(2H)-pyridazinedicarboxylate is thus obtained.

Proton NMR Spectrum In DMSO, at 300 MHz, chemical shifts of the peaks in ppm and multiplicity: 1.5 (m, 2H); 1.81 (m, 2H); 2.52 (m, 2H); 2.28 (m, 2H); 3.17 and 4.09 (m, 2H); 3.49 (m, 2H); 5.05 and 5.21 (m, 2H); 6.07 (m, 1H); 6.97 to 8.87 (m, 14H); 8.87 (broad s, 1H).

Example 17

The process is performed as in example 16, replacing, in step B, 3-bromopropanoyl chloride par 4-morpholine acid chloride and, in step D, the commercial (cyanoaminomethyl) benzene with the amine obtained in example 3.

The compound corresponding to (phenylmethyl) (3S)-3-[[[cyano(3-phenoxyphenyl)methyl]amino]-2-[(4-morpholin-yl)carbonyl]]tetrahydro-1(2H)-pyridazinecarboxylate is thus obtained.

Proton NMR Spectrum In CDCl$_3$, at 300 MHz, chemical shifts of the peaks in ppm and multiplicity: 1.53 and 1.70 (m, 2H); 1.80 and 1.93 (m, 2H); 3.12 and 3.24 (m, 4H); 3.40 (m, 4H); 4.34 (broad s, 1H); 5.05 and 5.17 (m, 2H) i 6.10 (broad s, 1H); 6.98 to 7.49 (m, 14H)

Example 18

The compound obtained in example 17 is deprotected by hydrogenation as indicated in example 5.

A compound corresponding to (3S)-N-[cyano(3-phenoxyphenyl)methyl]-2-[(4-morpholinyl)carbonyl]hexahydro-3-pyridazinecarboxamide is thus obtained.

Proton NMR Spectrum In CDCl$_3$, at 300 MHz, chemical shifts of the peaks in ppm and multiplicity: 1.57 and 1.76 (m, 2H); 1.83 and 2.14 (m, 2H); 2.77 and 2.98 (m, 2H); 3.31 and 3.48 (m, 4H); 3.62 (m, 4H); 4.52 (m, 1H); 6.09 (m, 1H); 6.95 to 7.4 (m, 9H)

Example 19

The process is performed as in example 16, replacing, in step B, 3-bromopropanoyl chloride with 4-morpholine acid chloride.

A compound corresponding to (phenylmethyl) (3S)-3-[[(cyanophenylmethyl)amino]carbonyl]-2-(4-morpholinylcarbonyl)tetrahydro-1(2H)-pyridazinedicarboxylate is thus obtained.

Proton NMR Spectrum In CDCl$_3$, at 300 MHz, chemical shifts of the peaks in ppm and multiplicity: 1.60 and 1.75 (m, 2H); 1.85 and 2.35 (m, 2H); 3.64 and 3.50 (m, 4H); 3.29 and 3.43 (m, 4H); 3.36 and 3.96 (m, 1H); 3.38 and 4.07 (m, 1H); 4.66 and 4.92 (m, 1H); 5.23 and 5.27 (m, 1H); 6.04 (m, 1H); 7.4 (m, 10H).

Example 20

The compound obtained in example 19 is deprotected by hydrogenation as indicated in example 5.

A compound corresponding to (3S)-N-[cyanophenylmethyl]-2-[(4-morpholinyl)carbonyl]hexahydro-3-pyridazine-carboxamide is thus obtained.

Proton NMR Spectrum In CDCl$_3$, at 300 MHz, chemical shifts of the peaks in ppm and multiplicity: 1.83 to 3.30 (m, 6H); 3.35 (m, 4H); 3.67 (m, 4H); 4.7 (m, 1H); 6.14 (m, 1H); 7.4 (m, 5H)

Example 21

The process is performed as in example 16, replacing, in step B, the 3-bromopropanoyl chloride with 4-morpholine acid chloride and, in step D, the commercial (cyanoaminomethyl)benzene with cyanoaminomethane.

A compound corresponding to (phenylmethyl) (3S)-3-[[[cyano(3-phenoxyphenyl)methyl]amino]-2-[(4-morpho-li-nyl)carbonyl]]tetrahydro-1(2H)-pyridazinecarboxylate is thus obtained.

MS (Positive electrospray) m/z:[MH]$^+$=415

Example 22

The process is performed as in example 16, replacing, in step B, the 3-bromopropanoyl chloride with 4-morpholine acid chloride and, in step D, the commercial (cyanoaminomethyl)benzene with 1-cyano-1-aminocyclohexane.

A compound corresponding to (phenylmethyl) (3S)-3-[[(1-cyanocyclohexyl)amino]carbonyl]-2-[(4-morpholinyl)-carbonyl]tetrahydro-1(2H)-pyridazinecarboxylate is thus obtained.

Proton NMR Spectrum In DMSO, at 300 MHz, chemical shifts of the peaks in ppm and multiplicity: 1.20 to 2.15 (m, 12H); 1.76 and 2.02 (m, 2H); 3.17 and 3.33 (m, 4H); 3.51 (m, 4H); 3.50 and 3.92 (m, 2H); 4.33 (broad s, 1H); 5.0 to 5.25 (m, 2H); 7.36 (m, 5H)

Example 23

The compound obtained in example 22 is deprotected by hydrogenation as indicated in example 5.

A compound corresponding to (3S)-N-(1-cyanocyclohexyl]-2-[(4-morpholinyl)carbonyl]hexahydro-3-pyridazine-carboxamide is thus obtained.

Proton NMR Spectrum In CDCl$_3$, at 300 MHz, chemical shifts of the peaks in ppm and multiplicity: 1.32 to 1.62 (m, 2H); 1.47 to 1.62 (m, 2H); 1.62 to 1.97 (m, 2H); 1.67 (m, 2H); 1.72 to 2.31 (m, 3H); 1.83 to 2.24 (m, 2H); 1.83 to 2.24 (m, 2H); 2.92 to 3.14 (m, 2H); 3.43 to 3.56 (m, 4H); 3.70 (m, 4H); 4.56 (broad s, 1H)

Example 24

Step A

The compound obtained in step A of example 16 is deprotected as indicated in example 5, to obtain the compound corresponding to methyl (3S)-2-[(4-morpholinyl)carbonyl]tetrahydro-1(2H)-pyridazine-carboxylate.

Step B 200 mg (0.8 mmol) of ester dissolved in 5 ml of DMF, at 0° C., are added dropwise to a solution of 5 ml of DMF containing 100 mg (0.002 mol) of NaH. After warming the mixture to room temperature, 320 ml (5 mmol) of methyl iodide are added. The reaction medium is stirred for 15 hours at 100° C. The medium is poured into 25 ml of water and then extracted with 25 ml of ethyl acetate. The organic phase is dried and then concentrated. After purification by flash chromatography, 125 mg of an oil corresponding to methyl (3S) -2-[(4-morpholinyl)carbonyl]-1-methyl-tetrahydro-1 (2H)-pyridazinecarboxylate are obtained.

The corresponding yield is 60%. Proton NMR Spectrum In DMSO, at 300 MHz, chemical shifts of the peaks in ppm and multiplicity: 1.38, 1.76 and 1.84 (broad s, 4H); 2.50 (m, 3H); 2.81 and 2.91 (m, 2H); 3.33 (m, 4H); 3.53 (m, 4H); 3.56 (s, 3H); 4.04 (broad s, 1H)

Step C

The product obtained in step B is saponified as indicated in Step B of example 2.

Proton NMR Spectrum In DMSO, at 300 MHz, chemical shifts of the peaks in ppm and multiplicity: 1.51 and 1.61 (m, 1H); 1.83 (m, 2H); 2.53 (s, 3H); 2.86 (m, 2H); 3.36 (m, 4H); 3.55 (m, 4H); 4.02 (t, 1H)

Step D

The process is performed with the product obtained in step C as indicated in Step D of example 16, replacing the commercial (cyanoaminomethyl)benzene with the amine obtained in example 3.

The product corresponding to (3S)-N-[cyano(3-phenoxyphenyl)methyl]-1-methyl-2-[(4-morpholinyl)-carbonyl] hexahydro-3-pyridazinecarboxamide is thus obtained.

MS (Positive electrospray) m/z: [MH]$^+$=464

Example 25

Step A

This step is identical to that of example 24.

Step B 400 mg of potassium carbonate (2.72 mmol) are added to a solution of 3 ml of DMF containing 200 mg (0.8 mmol) of ester. The mixture is brought to 100° C. 322 ml (2.4 mmol) of benzyl bromide are added. The mixture is stirred for 15 hours at 100° C. The medium is poured into 25 ml of water and then extracted with 25 ml of ethyl acetate. The organic phase is dried and then concentrated. After purification by flash chromatography, 158 mg of oil corresponding to methyl (3S)-2-[(4-morpholinyl)carbonyl]-1-phenylmethyl-tetrahydro-1(2H)-pyridazinecarboxylate is recovered.

The corresponding yield is 59%. MS (Positive electrospray) m/z: [MH]$^+$: 348

Step C

The product obtained in step C is saponified as indicated in step B of example 2 and the corresponding carboxylic acid is obtained.

The corresponding yield is 91%. MS (Positive electrospray) m/z: [MH]$^+$: 334

Step D

The process is performed with the product obtained in step C as indicated in step D of example 16, replacing the commercial (cyanoaminomethyl)benzene with the amine obtained in example 3.

The product (mixture of 2 diastereoisomers) corresponding to (3S)-N-[cyano(3-phenoxyphenyl)methyl]-1-(phenylmethyl)-2-[(4-morpholinyl)carbonyl]hexahydro-3-pyridazinecarboxamide is thus obtained. The 2 diastereoisomers are separated by flash chromatography.

28 mg of isomer A and 16.5 mg of isomer B are obtained (overall yield=27%). Proton NMR Spectrum In DMSO, at 300 MHz, chemical shifts of the peaks in ppm and multiplicity: First isomer: 1.63 to 1.77 (m, 2H); 1.94 (m, 2H); 2.78 (m, 2H); 3.29 (m, 4H); 3.51 (t, 4H); 3.84 (m, 1H); 3.91 (m, 2H); 3.99 (m, 1H); 4.20 (m, 1H); 6.08 and 6.16 (d, 1H); 6.98 to 7.42 (m, 14H); 8.91 and 9.00 (broad s, 1H). Second isomer: 1.62 to 1.77 (m, 2H); 1.94 (m, 2H); 2.78 (m, 2H); 3.30 (m, 4H); 3.51 (m, 4H); 3.84 (m, 1H); 3.92 (m, 2H); 4.01 (m, 1H); 4.20 (m, 1H); 6.08 and 6.16 (d, 2H); 6.98 to 7.42 (m, 14H); 8.91 and 9.00 (broad s, 1H).

Example 26

Pharmacological study of the products of the invention Study of the inhibition of cathepsin K The test products (10 mM) are diluted to 1 mM in DMSO and distributed in polystyrene Nunc 96-well plates at a rate of 2 µl per well. Column 12 of the plate is reserved for the controls and thus receives 1 µl of DMSO (without products) per well. The plates are stored at −80° C. and thawed on the day of the experiment.

The products are diluted to 50 μM by addition of 38 μl of reaction buffer: 100 mM sodium acetate, 5 mM EDTA, 1 mM DTT, pH 5.5. The addition and all the pipetting are performed with a 96-tip CybiWell pipette. After mixing the solutions, each product is transferred into 2 wells (duplicates) of a black Greiner 384-well plate at a rate of 10 μl per well. Two 96-well plates can thus be tested in one 384-well plate.

A solution of substrate, Z-Val-Arg-AMC (Calbiochem), at a concentration of 50 μm is prepared in the reaction buffer. The substrate is the distributed among all the wells of the 384-well plate (20 μl per well).

A solution of cathepsin K at a concentration of 12.5 ng/ml is prepared in the reaction buffer and distributed among all the wells of the 384-well plate (20 μl per well) except for the 16 wells serving as 100% inhibition controls (columns 23 and 24, lines I to P), which receive 20 μl of enzyme-free buffer. The 100% inhibition controls are performed in columns 23 and 24, lines A to H, which contain no products.

The plates are then incubated for two hours at room temperature, and then read on a Fluoroskan (Labsystems): excitation 390 nm; emission 460 nm.

The final concentrations of each of the reagents are: Products 10 μM, Substrate 20 μM, enzyme 5 ng/ml.

The percentages of inhibition for each of the products are calculated by using the points at 0 and 100% inhibition of each plate as references. The products showing significant inhibition are then retested over a concentration range from 50 to 0.5 μM to determine an IC50.

Results

The IC50 values found for certain products are given in table I below, in micromoles:

TABLE I

| Example | IC$_{50}$ (μM) |
|---|---|
| 4 | 1–10 |
| 5 and 6 | <1 |
| 7 | 1–10 |
| 8 | 1–10 |
| 9 | 1–10 |
| 10 | 1–10 |
| 11 | 1–10 |
| 12 | 1–10 |
| 13 | 1–10 |
| 14 | 1–10 |
| 15 | <1 (2 values) |

Example 25

Pharmaceutical Composition

Tablets corresponding to the following formula were prepared:
Compound of Example 1 . . . 500 mg
Excipient for a finished tablet weighing . . . 1 g (details of the excipient: lactose, talc, starch, magnesium stearate).

What is claimed is:
1. A compound of formula (I):

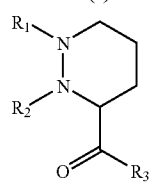

wherein:
$R_1$ is hydrocen, linear or branched alkyl containing from 1 to 6 carbon atoms, —COR or —COOR, wherein R is chosen from:
linear or branched alkyl containing from 1 to 6 carbon atoms, optionally substituted with pyridyl or carbamoyl,
linear or branched —CH$_2$-alkenyl containing in total from 3 to 9 carbon atoms, or
aryl containing from 6 to 10 carbon atoms or aralkyl containing from 7 to 11 carbon atoms, wherein the arly and aralkyl are independently optionally substituted with OH, NH$_2$, NO$_2$, linear or branched alkyl containing from 1 to 6 carbon atoms, linear or branched alkoxy containing from 1 to 6 carbon atoms, or 1 to 3 halogen atoms,
$R_2$ is a group corresponding to formula (II) below:

wherein
n is 0, 1, 2 or 3; a double bond possibly being present when n is 2 or 3;
X is one of the following groups:
saturated or unsaturated monocyclic or bicyclic heterocyclic group;
aryl containing from 6 to 10 carbon atoms or aralkyl containing from 7 to 11 carbon atoms, wherein the aryl and aralkyl are independently optionally substituted with OH, NH$_2$, NO$_2$, linear or branched alkyl containing from 1 to 6 carbon atoms, linear or branched alkoxy containing from 1 to 6 carbon atoms, or 1 to 3 halogen atoms;
—NR$_4$R$_5$, wherein R$_4$ is linear or branched alkyl containing from 1 to 6 carbon atoms, —COR,
—CONHR, —CSNHR or —SO$_2$R, R having the meaning given above, and R$_5$ is hydrogen or linear or branched alkyl containing from 1 to 6 carbon atoms; or
—COR, R having the meaning given above,
$R_3$ is —Y—(CH$_2$)$_m$—C(CN)R$_6$R$_7$, wherein:
Y is oxygen or —N(R$_8$)—,
R$_8$ is hydrogen or linear or branched alkyl containing from 1 to 6 carbon atoms,
m is 0, 1, 2 or 3,
R$_6$ is hydrogen, linear or branched alkyl containing from 1 to 6 carbon atoms, aryl or aralkyl group, wherein the aryl and aralkyl are independently optionally substituted with OH, NH$_2$, NO$_2$, linear or branched alkyl containing from 1 to 6 carbon atoms, linear or branched alkoxy containing from 1 to 6 carbon atoms, or aryloxy of 7 to 11 carbon atoms, wherein the aryloxy is optionally substituted with 1 to 3 halogen atoms; and
R$_7$ is hydrogen or linear or branched alkyl containing from 1 to 6 carbon atoms, or R$_6$ and R$_7$ taken together with the carbon to which they are attached form cyclohexyl, or
a racemic, enantiomeric or diastereoisomeric form thereof; or an addition salt thereof.

2. The compound of claim 1, wherein R$_1$ is hydrogen, methyl, benzyl, —COO-benzyl or —CO-methylenebenzyl.

3. The compound of claim 1, wherein n is equal to 0 or 2.

4. The compound of claim 1, wherein X is —NR₄R₅ and R₅ is hydrogen.

5. The compound of claim 1, wherein X is phenyl or —NHCO-benzyl.

6. The compound of claim 1, wherein X is

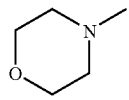

7. The compound of claim 1, wherein R₈ is hydrogen.

8. The compound of claim 1, wherein R₇ is hydrogen.

9. The compound of claim 1, wherein R₆ is hydrogen.

10. The compound of claim 1, wherein R₆ is phenyl, —C₆H₄—O—C₆H₅ or —C₂H₄—O—C₆H₄Br.

11. The compound of claim 1, wherein m is equal to 0 or 2.

12. The compound of claim 1, having the following stereochemical formula:

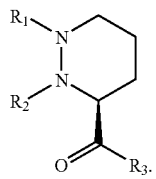

13. The compound of claim 1, which is
(3S)-2-[3-[(phenylacetyl)amino]-1-oxopropyl]-N-[cyano (3-phenoxyphenyl)methyl]hexahydro-3-pyridazinecarboxamide, or
(3S)-N-[cyano(3-phenoxyphenyl)methyl]-2-(1-oxo-3-phenylpropyl)hexahydro-3-pyridazinecarboxamide.

14. A pharmaceutical composition comprising a pharmaceutically acceptable amount of the compound of claim 1 and a pharmaceutically acceptable support.

15. A process for preparing the compound of claim 1, comprising wherein it reacting a compound of formula (IV)

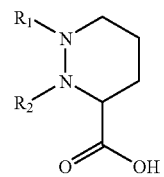

wherein R₁ and R₂ are definefd as in claim 1,
with an aminonitrile or cyanohydrin of formula HR₃, wherein R₃ is defined as in claim 1, to yield the compound of formula (I).

16. The process of claim 15, wherein the compound of formula (IV) is prepared comprising
(1) reacting a compound of formula (II)

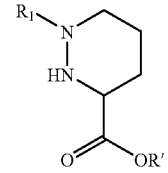

with an acid chloride of formula R₂Cl, wherein:

wherein;
R₁ is hydrogen, linear or branched alkyl containing from 1 to 6 carbon atoms, —COR or —COOR, wherein R is chosen from:
  linear or branched alkyl containing from 1 to 6 carbon atoms, optionally substituted with pyridyl or carbamoyl,
  linear or branched —CH₂-alkenyl containing in total from 3 to 9 carbon atoms, or
  aryl containing from 6 to 10 carbon atoms or aralkyl containing from 7 to 11 carbon atoms, wherein the aryl and aralkyl are independently optionally substituted with OH, NH₂, NO₂, linear or branched alkyl containing from 1 to 6 carbon atoms, linear or branched alkoxy containing from 1 to 6 carbon atoms, or 1 to 3 halogen atoms,
R₂ is a group corresponding to formula (II) below:

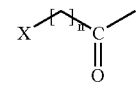

wherein
n is 0, 1, 2 or 3; a double bond possibly being present when n is 2 or 3;
X is one of the following groups:
saturated or unsaturated monocyclic or bicyclic heterocyclic group;
aryl containing from 6 to 10 carbon atoms or aralkyl containing from 7 to 11 carbon atoms, wherein the aryl and aralkyl are independently optionally substituted with OH, NH₂, NO₂, linear or branched alkyl containing from 1 to 6 carbon atoms, linear or branched alkoxy containing from 1 to 6 carbon atoms, or 1 to 3 halogen atoms;
—NR₄R₅, wherein R₄ is linear or branched alkyl containing from 1 to 6 carbon atoms, —COR,
—CONHR, —CSNHR or —SO₂R, R having the meaning given above, and R₅ is hydrogen or linear or branched alkyl containing from 1 to 6 carbon atoms; or
—COR, R having the meaning given above, and
R'is a linear or branched alkyl group containing from 1 to 6 carbon atoms, to yield a compound of formula (III):

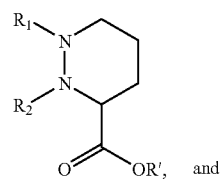

(2) hydrolyzing the compound of formula (III) to yield the compound of formula (IV).

17. The process of claim 15, further comprising subjecting the compound of formula I to hydrogenolysis.

18. A method for treating osteoporosis, hypercalcaemia, osteopenia, gingival disease, rheumatoid arthritis, or Paget's disease in a patient in need thereof, comprising administering to the patient a pharmaceutically effective amount of the compound according to claim 1.

19. The compound according to claim 1, wherein R₆ is phenyl.

* * * * *